United States Patent [19]

Lewis et al.

[11] 4,263,451

[45] Apr. 21, 1981

[54] REMOVING CARBONACEOUS CONTAMINANT FROM ZINC OXIDE

[75] Inventors: Ronnie L. Lewis; Fred T. Sherk, both of Bartlesville, Okla.

[73] Assignee: Phillips Petroleum Company, Bartlesville, Okla.

[21] Appl. No.: 85,172

[22] Filed: Oct. 15, 1979

[51] Int. Cl.$^3$ .................. C07C 63/26; C07C 63/08
[52] U.S. Cl. ........................... 562/481; 260/429.9; 252/416; 252/419; 423/622; 423/623; 562/482
[58] Field of Search ............... 423/107, 622, 623; 252/416; 260/429.9; 562/481

[56] References Cited

U.S. PATENT DOCUMENTS

| | | | |
|---|---|---|---|
| 1,426,349 | 8/1922 | Booge | 423/622 |
| 3,251,653 | 5/1966 | Aditya | 422/193 |
| 3,261,863 | 7/1966 | Schenk | 562/482 |
| 3,406,228 | 10/1968 | Hardy | 423/622 |
| 3,607,065 | 9/1971 | Forseth | 423/458 |
| 3,681,031 | 8/1972 | Johnson | 422/157 |
| 3,776,930 | 12/1973 | Wu | 260/429.9 |
| 3,873,609 | 3/1975 | Wu | 562/481 |
| 3,875,218 | 4/1975 | Wu | 562/481 |
| 3,989,804 | 11/1976 | Vanderveen | 423/457 |

*Primary Examiner*—Brian E. Hearn

[57] ABSTRACT

A method for removing carbonaceous impurity from zinc oxide by contacting a water slurry of contaminated zinc oxide with oxygen in a reactor at reaction conditions sufficient to produce oxide products of the carbon contaminants and passing the reactor effluent through a filter to collect solid zinc oxide while passing the oxides of carbon through the filter. In a preferred embodiment, contaminated zinc oxide separated from the reaction product in the preparation of terephthalic acid from benzoic acid using zinc benzoate catalyst is subjected to treatment for removal of carbonaceous contaminants before being recycled to reaction with molten benzoic acid to produce zinc benzoate catalyst used in the reaction.

4 Claims, 1 Drawing Figure

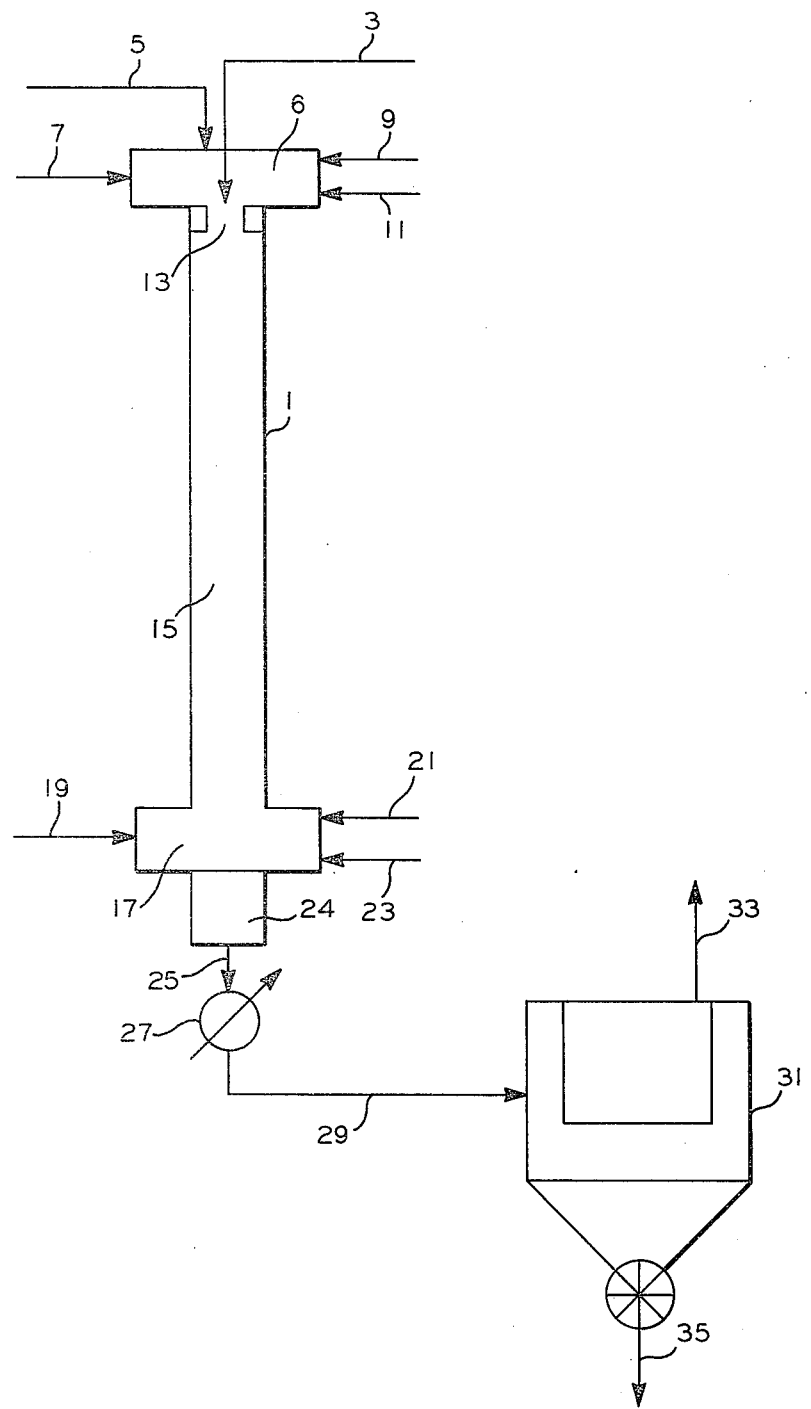

REMOVING CARBONACEOUS CONTAMINANT FROM ZINC OXIDE

BACKGROUND OF THE INVENTION

This invention relates to removing carbonaceous impurities from zinc oxide. In one of its aspects, this invention relates to the oxidation of carbonaceous contaminants. In another of its aspects, this invention relates to an improvement in the process for preparing terephthalic acid from benzoic acid using zinc benzoate catalyst.

In the process disclosed in U.S. Pat. No. 3,873,609 for making terephthalic acid from benzoic acid using zinc benzoate catalyst, incorporated herein by reference, the catalyst is decomposed to zinc oxide by contact with quench water on the outlet of the reactor. This zinc oxide is insoluble in the effluent stream and eventually emerges in the process along with carbon residue to be slurried with terphenyl and passed to reaction with molten benzoic acid to be regenerated as zinc benzoate catalyst. In such a recycled system, there is a constant build-up of carbonaceous contaminant which must be removed to prevent interference with the reaction and coloration of product made with contaminated catalysts.

It is well known to remove the carbon contaminant by filtering the zinc benzoate solution. It has been found, however, that such a filtration is very difficult. It must be performed at temperatures above 300° F. because the terphenyl in which the zinc benzoate is dissolved solidifies well above room temperature. Filter blinding on this operation can be a major problem.

The present invention has been found to solve the problem of removal of carbonaceous contaminant from zinc oxide.

It is therefore an object of this invention to provide a method for removing carbonaceous contaminant from zinc oxide. It is another object of this invention to provide a process for the recycle of zinc oxide for the preparation of zinc benzoate with an efficient and economical removal of carbonaceous contaminant.

Other aspects, objects and the various advantages of this invention will become apparent upon reading the specification and the appended claims.

STATEMENT OF THE INVENTION

According to this invention, a method is provided for removing carbonaceous impurity from a mixture with zinc oxide. In the method, a water slurry of carbonaceous impurity-contaminated zinc oxide is contacted with oxygen in a reactor under conditions sufficient to produce an effluent comprising zinc oxide and oxides of carbon with the effluent from the reaction then passed through a filter to collect the solid zinc oxide on the filter surface while the gaseous oxides of carbon pass through the filter.

In an embodiment of the invention, a stream containing zinc oxide and carbon residue produced by water quenching of the reaction effluent from the reaction of potassium benzoate in the presence of a zinc benzoate catalyst is subjected to contact with oxygen in a reactor under conditions sufficient to produce an effluent containing oxides of carbon and zinc oxide, the zinc oxide is separated from the effluent by filter means and the zinc oxide is contacted with molten benzoic acid to produce zinc benzoate which is recycled as catalyst.

Any conventional roaster or combustion zone designed to handle solids is suitable for carrying out the oxidation step. Supplementary fuels such as natural gas may be required to maintain the necessary temperature, above 2000° F., in a range of about 2000° F. to about 3000° F., preferably 2300° F. to 2800° F., to burn the carbon. An excess of air should be maintained in the combustion zone to provide the oxygen necessary for the oxidation. A device that has been found especially suitable for carrying out the combustion is a carbon black reactor. Most preferred is a carbon black reactor such as a tangential reactor as described in U.S. Pat. No. 3,607,065, which attains the required reaction temperature in the reactor tunnel portion of the reactor.

The effluent from the combustion zone is typically passed through any of the well known filtering apparatuses used in carbon black production, particularly bag filters, to collect the solid zinc oxide while the gaseous products are allowed to pass through the filter element.

BRIEF DESCRIPTION OF THE DRAWING

A typical operation of the invention is best understood in conjunction with the drawing which is a schematic flow of material to be treated through an oxidation reactor and a bag filtering operation.

Referring now to the drawing, a typical carbon black reactor (1) is used for the oxidation reaction. A water slurry containing zinc oxide and carbonaceous contaminant (3) and combustion fuel (5) are fed axially into a primary combustion zone (6) where they are mixed with tangential flows (7), (9) of mixed air and combustion fuel and an additional flow of oxygen (11), which is optional. Here additional oxygen is supplied, but could be eliminated by use of increased temperature of air and combustion fuel entering the combustion zone. The mixture of gases passes through a choke zone (13) into the reaction tunnel (15) and into a secondary combustion chamber (17) where there is further mixing with tangential flow of air and combustion gas (19), (21) and oxygen (23). The reactor effluent passes through reactor exit section (24) and line (25), is cooled in a heat recovery unit (27) and passes through line (29) into a bag house (31). Off gas passes through line (33). The zinc oxide with some residual carbon contamination is collected in bag house (31) and passed through line (35) to storage or recycle in a reaction system such as the production of terephthalic acid from benzoic acid using a zinc benzoate catalyst.

The reaction system operated by the method of this invention is integrated into a terephthalic acid production system by using a water slurry of zinc oxide from which potassium terephthalate has been removed as the slurry feed in line (3) and by returning the zinc oxide from line (35) to be dissolved in terphenyl and reacted with molten benzoic acid to produce a zinc benzoate catalyst for the terephthalic acid product. Refer here to U.S. Pat. No. 3,873,609 which is incorporated herein by reference. The method of this invention is used in the terephthalic acid process to prevent the continuous build-up of carbonaceous contaminant in the catalyst recycle system.

The following example illustrates the potential of a carbon black-type reactor for use in recovery of zinc oxide by the process of this invention:

EXAMPLE I

A small refractory-lined tangential carbon black reactor was operated on a water slurry consisting of 2.5 wt.

% ZnO and 2.5 wt. % carbon black to simulate catalyst residue from a TPA plant. Reactor inside dimensions were as follows (in inches):

| | |
|---|---|
| Primary Combustion Chamber (6) | 5 in. dia. × 3 in. |
| Choke (13) | 1 in. dia. × 1 in. |
| Reactor Tunnel (15) | 2¼ in. dia. × 32 in. |
| Secondary Combustion Chamber (17) | 5 in. dia. × 3 in. |
| Exit Section (24) | 2¼ in. dia. × 5 in. |

Operating conditions for a typical run were as follows:

| Primary Combustion Chamber (6) | |
|---|---|
| Flow Rates, 1/min | |
| Tangential Air | 170 |
| Tangential Gas | 8.5 |
| Axial Gas | 12.5 |
| Oxygen | 12.5 |
| Temperatures, °C. | |
| Chamber | 1,290 |
| Choke | 1,480 |
| Tunnel | 1,385 |
| Secondary Combustion Chamber (17) | |
| Flow Rates, 1/min | |
| Tangential Air | 127 |
| Tangential Gas | 10.6 |
| Temperatures, °C. | |
| Chamber | 1,225 |
| Outlet | 1,020 |
| Feed rate, ml/min | 10 |
| Product, % ZnO | 88 |
| Residence Time, sec. | 0.12 |

This example shows that carbonaceous contaminant associated with solid zinc oxide can be successfully removed by the use of a carbon black reactor. Adjustment of the operating conditions can result in the recovery of nearly pure zinc oxide from such a reactor.

We claim:

1. A method for removing carbonaceous impurity from a mixture with zinc oxide, said method comprising:
   (a) contacting a water slurry of zinc oxide contaminated with carbonaceous impurity in a reaction zone with oxygen under conditions sufficient to produce an effluent comprising zinc oxide and oxides of carbon, and
   (b) passing the effluent from the reaction through a filter to collect solid zinc oxide while the oxides of carbon pass through the filter.

2. A method of claim 1 wherein the contact with oxygen is made at a temperature in a range above 2000° F.

3. A method of claim 2 wherein said contact with oxygen is made at a temperature within the range of about 2000° F. to about 3000° F.

4. In the reaction of potassium benzoate in the presence of a zinc benzoate catalyst to produce terephtholic acid in which water quenching of the reaction effluent produces a slurry stream containing a mixture of zinc oxide and carbonaceous impurity,
   a method for regenerating zinc benzoate catalyst from said zinc oxide containing stream comprising:
   (a) removing said carbonaceous impurity from the mixture with zinc oxide by contacting the water slurry in a reaction zone with oxygen under conditions sufficient to produce an effluent comprising zinc oxide and oxides of carbon and passing the resultant effluent from this reaction through a filter to collect solid zinc oxide while the oxides of carbon pass through the filter to provide zinc oxide of at least reduced carbonaceous impurity content, and
   (b) contacting said zinc oxide with molten benzoic acid thereby producing zinc benzoate.

* * * * *